United States Patent
Toida (10) Patent No.: US 7,924,428 B2
(45) Date of Patent: Apr. 12, 2011

(54) OPTICAL ROTARY ADAPTOR AND OPTICAL TOMOGRAPHIC IMAGING APPARATUS USING THE SAME

(75) Inventor: Masahiro Toida, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 196 days.

(21) Appl. No.: 12/411,098

(22) Filed: Mar. 25, 2009

(65) Prior Publication Data
US 2009/0244545 A1   Oct. 1, 2009

(30) Foreign Application Priority Data
Mar. 26, 2008   (JP) ................................ 2008-081547

(51) Int. Cl.
*G01B 9/02* (2006.01)

(52) U.S. Cl. ......................................... 356/479; 385/25

(58) Field of Classification Search .................. 356/479, 356/477; 600/478; 385/25
See application file for complete search history.

(56) References Cited

U.S. PATENT DOCUMENTS

| | | | |
|---|---|---|---|
| 6,668,185 B2 | 12/2003 | Toida | |
| 7,382,949 B2 * | 6/2008 | Bouma et al. | 385/25 |
| 2004/0109164 A1 * | 6/2004 | Horii et al. | 356/479 |
| 2004/0109636 A1 * | 6/2004 | Korn | 385/25 |
| 2005/0168751 A1 * | 8/2005 | Horii et al. | 356/479 |
| 2008/0024788 A1 | 1/2008 | Shimizu et al. | |
| 2008/0031410 A1 | 2/2008 | Shimizu et al. | |
| 2008/0252901 A1 | 10/2008 | Shimizu et al. | |

FOREIGN PATENT DOCUMENTS

| | | |
|---|---|---|
| JP | 2002-200037 A | 7/2002 |
| JP | 2005-156540 A | 6/2005 |
| WO | 2005/031320 A1 | 4/2005 |

* cited by examiner

*Primary Examiner* — Tarifur Chowdhury
*Assistant Examiner* — Jonathan M Hansen
(74) *Attorney, Agent, or Firm* — Sughrue Mion, PLLC (57) ABSTRACT

An optical rotary adapter is featured by including: a fixed side optical fiber which is fixedly supported by a fixed sleeve and which has an end surface inclined with respect to a plane perpendicular to the optical axis of the optical fiber; a fixed side collimator lens which is arranged to be separated from the inclined end surface of the fixed side optical fiber by a predetermined interval; a rotation side optical fiber which is fixedly supported substantially at the center of a rotatably supported rotary cylinder, which is arranged to face the fixed side collimator lens, and which has an end surface inclined with respect to a plane perpendicular to the optical axis of the fixed side collimator lens; a rotation side collimator lens which is fixedly supported by the rotary cylinder, and which is arranged between the fixed side collimator lens and the rotation side optical fiber so as to be separated from the inclined end surface of the rotation side optical fiber by a predetermined interval; a second luminous flux optical fiber which guides a second luminous flux having a function different from that of a first luminous flux as a measuring light beam to the inside of the fixed sleeve; and a multiplexing device which is provided between the fixed side collimator lens and the rotation side collimator lens, and which multiplexes the first luminous flux with the second luminous flux.

10 Claims, 8 Drawing Sheets

OPTICAL ROTARY ADAPTOR AND OPTICAL TOMOGRAPHIC IMAGING APPARATUS USING THE SAME

BACKGROUND OF THE INVENTION

1. Field of the Invention

The present invention relates to an optical rotary adapter and an optical tomographic imaging apparatus using the optical rotary adapter. More particularly, the present invention relates to an optical rotary adapter configured to rotatably connect between optical fibers which, in order to acquire an optical tomographic image of a measuring object, guide a measuring light beam to the measuring object and guide a return light beam from the measuring object, and relates to an optical tomographic imaging apparatus which irradiates a measuring object with a light beam and which acquires an optical tomographic image of the measuring object from a return light beam reflected from the measuring object.

2. Description of the Related Art

Conventionally, there is known an optical tomographic imaging apparatus using an optical coherence tomography (OCT) measuring method as a method for acquiring a tomogram without cutting a measuring object, such as a living tissue.

The OCT measuring method is a kind of optical interferometric methods and is a measuring method which utilizes the fact that in the case where a light beam emitted from a light source is divided into a measuring light beam and a reference light beam, optical interference is detected only when the optical path lengths of the measuring light beam and the reference light beam coincide with each other within the coherence length of the light source.

Here, since the light beam used in the OCT measuring method is a near-infrared light beam which is not visually recognized, it is difficult to confirm which part of a measured region is actually exposed to the light beam. Thus, an aiming beam (aiming light beam) serving as a mark is used together with the measuring light beam (OCT signal light beam).

There are known, for example, a method in which the aiming light beam is multiplexed with the OCT signal light beam by an optical coupler outside an optical fiber interferometer (see, for example, Japanese Patent Application Laid-Open No. 2002-200037, and the like), and a method in which the aiming light beam is multiplexed with the OCT signal light beam by an optical coupler in an optical fiber interferometer (see, for example, Japanese Patent Application Laid-Open No. 2005-156540, and the like).

SUMMARY OF THE INVENTION

However, in the multiplexing characteristics of the optical coupler, the coupling efficiency is controlled by the proximate distance between the optical fiber cores. Thus, since the wavelength region of the near-infrared wavelength used in the OCT measuring method is separated from the wavelength region of the visible wavelength of the aiming light beam, it is difficult to secure desired coupling characteristics for both the wavelengths. For this reason, there is a problem that the coupling efficiency to the OCT signal light beam is reduced.

The present invention has been made in view of the above described circumstances. An object of the present invention is to provide an optical rotary adapter capable of reducing a signal loss at the time of multiplexing light beams having different wavelengths, such as, for example, the aiming light beam, and the OCT signal light beam, and to provide an optical tomographic imaging apparatus using the optical rotary adapter.

In order to achieve the above described object, according to a first aspect of the present invention, there is provided an optical rotary adapter including: a fixed sleeve; a fixed side optical fiber which is fixedly supported by the fixed sleeve and which has at one end thereof an end surface inclined by a predetermined angle with respect to a plane perpendicular to the optical axis of the fixed side optical fiber; a fixed side collimator lens which is arranged to be separated from the inclined end surface of the fixed side optical fiber by a predetermined interval; a rotary cylinder which is supported so as to be rotatable with respect to the fixed sleeve; a rotation side optical fiber which is fixedly supported substantially at the center of the rotary cylinder, which is arranged to face the fixed side collimator lens, and which has an end surface inclined by a predetermined angle with respect to a plane perpendicular to the optical axis of the fixed side collimator lens; a rotation side collimator lens which is fixedly supported by the rotary cylinder, and which is arranged between the fixed side collimator lens and the rotation side optical fiber so as to be separated from the inclined end surface of the rotation side optical fiber by a predetermined interval; a rotation drive device which rotationally drives the rotary cylinder; a second luminous flux optical fiber which guides a second luminous flux having a wavelength different from a wavelength of a first luminous flux as a measuring light beam, to the inside of the fixed sleeve; a second luminous flux collimator lens which is arranged so as to be separated from the end surface of the second luminous flux optical fiber by a predetermined interval; and a multiplexing device which is provided between the fixed side collimator lens and the rotation side collimator lens in the fixed sleeve, and which multiplexes the first luminous flux with the second luminous flux.

Thereby, since it is configured such that the light beams having different wavelengths are multiplexed with each other in the optical rotary adapter, it is possible to avoid the loss of the OCT signal light beam, which loss is caused in a multiplexing function section incorporated in a conventional optical fiber interferometer. Further, by inclining the end surface of the optical fiber with respect to the plane perpendicular to the optical axis of the optical fiber, it is possible to prevent regularly reflected light from being returned, while improving the S/N by reducing unnecessary reflected light in the OCT optical rotary adapter section.

Further, a second aspect of the present invention is featured in that the multiplexing device is configured to include at least one dichroic mirror which transmits one of the first luminous flux and the second luminous flux and which reflects the other luminous flux.

Thereby, it is possible to reduce the light loss which is caused in the case where the conventional optical fiber coupler is used.

Further, a third aspect of the present invention is featured in that the multiplexing device includes a device which, when the first luminous flux is multiplexed with the second luminous flux, compensates an optical axis shift so that the optical axis of the luminous flux after the multiplexing is prevented from being shifted from the optical axis of the first luminous flux before the multiplexing.

Thereby, it is possible to make the optical axis of the light beam made incident on the optical rotary adapter coaxial with the optical axis of the light beam emitted from the optical rotary adapter.

Further, a fourth aspect of the present invention is featured in that the device which compensates the optical axis shift is configured by two inclined surfaces which are arranged substantially on the optical axis of the first luminous flux so as to face each other at respective angles having the same magnitude in the opposite directions.

Further, a fifth aspect of the present invention is featured in that the device which compensates the optical axis shift is configured by a trapezoidal prism arranged substantially on the optical axis of the first luminous flux.

Thereby, it is possible to perform the multiplexing without the regularly reflected light beam of the first luminous flux being returned to the first luminous flux propagation path.

Further, a sixth aspect of the present invention is featured in that the optical axis shift is compensated by offsetting beforehand the position of the fixed side optical fiber so that the optical axis of the luminous flux after the multiplexing is prevented from being shifted from the optical axis of the first luminous flux before the multiplexing.

Thereby, it is possible to make the optical axis of the light beam made incident on the optical rotary adapter coaxial with the optical axis of the light beam emitted from the optical rotary adapter.

Further, a seventh aspect of the present invention is featured in that the second luminous flux is an aiming light beam serving as a measuring mark.

Thereby, it is possible to improve the visibility of the OCT measuring region by multiplexing the aiming light beam, and hence it is possible to perform accurate measurement while easily confirming the measuring region.

Further, an eighth aspect of the present invention is featured in that the second luminous flux is a laser light beam for medical treatment.

This makes it possible to apply the optical rotary adapter to a medical treatment apparatus having an OCT monitoring function.

Further, a ninth aspect of the present invention is featured in that the second luminous flux is a measuring light beam having a wavelength different from the wavelength of the first luminous flux.

This makes it possible to expand the wavelength band, and thereby it is possible to apply the optical rotary adapter to a multiple wavelength OCT apparatus.

Further, in order to similarly achieve the above described object, according to a tenth aspect of the present invention, there is provided an optical tomographic imaging apparatus which acquires an optical tomographic image of a measuring object, and which is featured by including: a first light source which emits a light beam for measurement; a second light source which emits a second luminous flux having a wavelength different from the wavelength of the light beam for measurement; a branching device which branches the light beam emitted from the first light source into a measuring light beam and a reference light beam; an optical probe including a rotation side optical fiber which guides the measuring light beam to the measuring object and which guides a return light beam from the measuring object, a measuring section which is arranged at the distal end section of the rotation side optical fiber and which irradiates the measuring object with the measuring light beam to acquire the return light beam, and a probe outer tube which covers the outer periphery of the rotation side optical fiber and the measuring section so as to rotatably hold the rotation side optical fiber and the measuring section, and in which at least a region transmitting the measuring light beam from the measuring section and the return light beam from the measuring object is made of a transparent material; a fixed side optical fiber which guides the measuring light beam to the rotation side optical fiber and which guides the return light beam guided by the rotation side optical fiber; the optical rotary adapter according to one of the first aspect to the ninth aspect, which rotatably connect the rotation side optical fiber to the fixed side optical fiber, which multiplexes the second luminous flux emitted from the second light source and guided by a second luminous flux optical fiber, with the first luminous flux as the measuring light beam, and which also transmits the multiplexed luminous flux and the return light beam; a multiplexing section which multiplexes the return light beam detected by the measuring section and guided via the optical rotary adapter with the reference light beam, so as to generate an interference light beam; an interference light detecting section which detects the interference light beam as an interference signal; and a tomographic image acquiring section which acquires the optical tomographic image from the interference signal detected by the interference light detecting section.

As a result, the aiming light beam is multiplexed by using the function which prevents the regularly reflected light beam from being returned while improving the S/N by reducing the unnecessary reflected light in the OCT optical rotary adapter section. Thereby, it is possible to avoid the loss of the OCT signal light beam which loss is caused in the aiming light multiplexing function section incorporated in the conventional optical fiber interferometer, and also it is possible to improve the visibility of the region subjected to the OCT measurement.

As described above, according to the present invention, light beams having different wavelengths are multiplexed with each other in the optical rotary adapter, and thereby, it is possible to avoid the loss of the OCT signal light beam which loss is caused in the multiplexing function section incorporated in the conventional optical fiber interferometer.

DETAILED DESCRIPTION OF THE PREFERRED EMBODIMENTS

In the following, an optical rotary adapter according to the present invention and an optical tomographic imaging apparatus using the optical rotary adapter will be described in detail with reference to the accompanying drawings.

Figure 1:
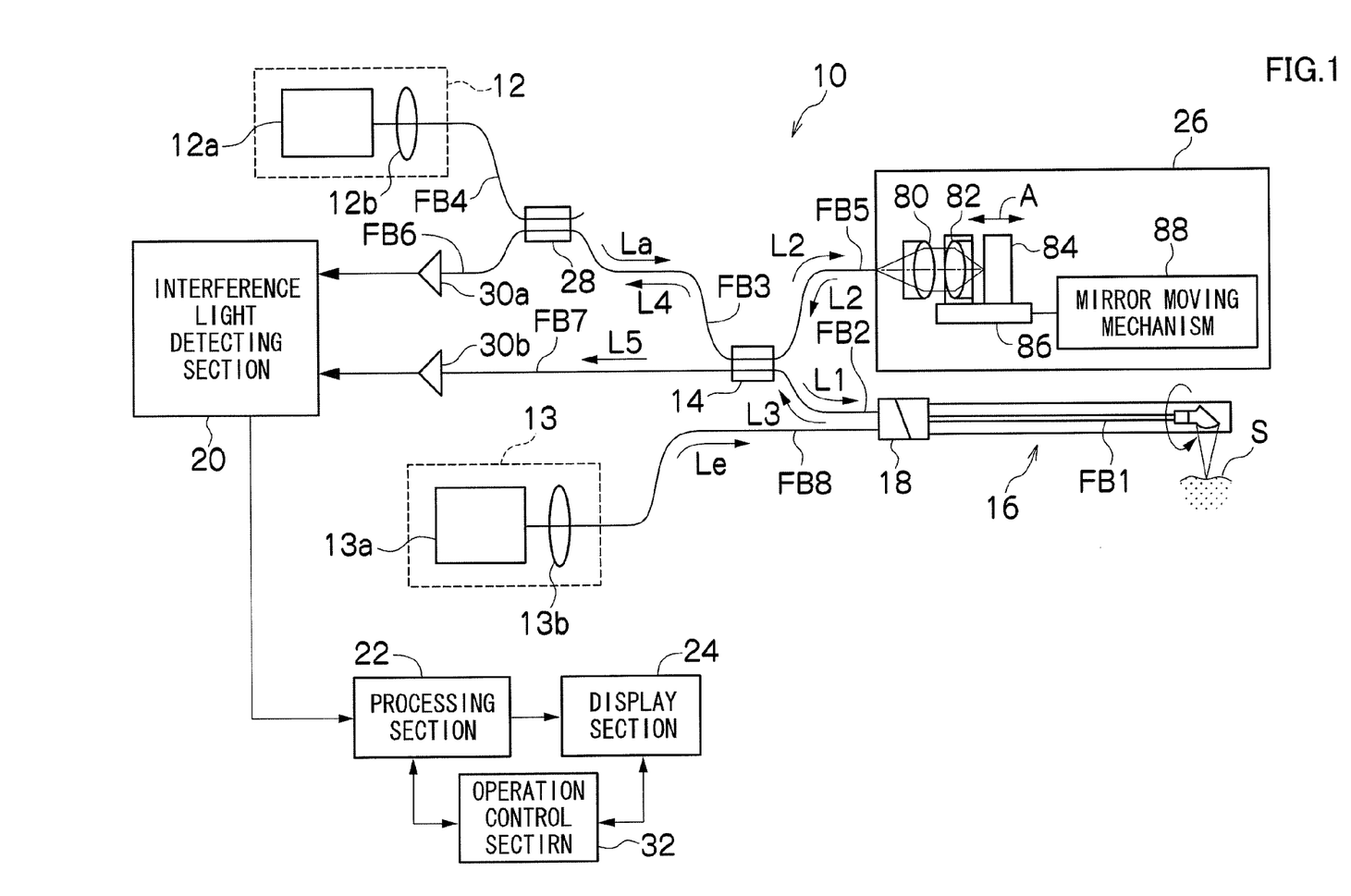
FIG. 1 is a block diagram showing a schematic configuration of a first embodiment of an optical tomographic imaging apparatus using an optical rotary adapter according to the present invention.

FIG. 1 is a block diagram showing a schematic configuration of a first embodiment of an optical tomographic imaging apparatus using an optical rotary adapter according to the present invention.

An optical tomographic imaging apparatus 10 according to the present invention shown in FIG. 1, which is used to acquire an optical tomographic image of a measuring object by an optical coherence tomography (OCT) measuring method, includes: a first light source (first light source unit) 12 which emits a light beam for measurement La; an optical fiber coupler (branching/multiplexing section) 14 which branches the light beam La emitted from the first light source 12 into a measuring light beam (first luminous flux) L1 and a reference light beam L2, and which multiplexes the reference light beam L2 with a return light beam L3 from a measuring object S as a subject, to generate an interference light beam L4; an optical probe 16 including a rotation side optical fiber FB1 which guides the measuring light beam L1 branched by the optical fiber coupler 14 to the measuring object, and which guides the return light beam L3 from the measuring object; a fixed side optical fiber FB2 which guides the measuring light beam L1 to the rotation side optical fiber FB1, and which guides the return light beam L3 guided by the rotation side optical fiber FB1; an optical rotary adapter 18 which rotatably connects the rotation side optical fiber FB1 to the fixed side optical fiber FB2, and which transmits the measuring light beam L1 and the return light beam L3; an interference detecting section 20 which detects, as an interference signal, the interference light beam L4 generated by the optical fiber coupler 14; a processing section 22 which acquires an optical tomographic image (hereinafter also referred to simply as "tomographic image") by processing the interference signal detected by the interference detecting section 20; and a display section 24 which displays the optical tomographic image acquired by the processing section 22.

Further, the optical tomographic imaging apparatus 10 includes: a second light source (second light source unit) 13 which emits an aiming light beam (second luminous flux) Le for indicating a measuring mark; an optical path length adjusting section 26 which adjusts the optical path length of the reference light beam L2; an optical fiber coupler 28 which spectrally diffracts the light beam La emitted from the first light source 12; detecting sections 30a and 30b which detect return light beams L4 and L5 multiplexed by the optical fiber coupler 14; and an operation control section 32 which inputs various conditions to the processing section 22, the display section 24, and the like, and which performs the change of settings, and the like.

Note that, as will be described below, in the optical tomographic imaging apparatus 10 shown in FIG. 1, various optical fibers FB (FB3, FB4, FB5, FB6, FB7, FB8, and the like), including the rotation side optical fiber FB1 and the fixed side optical fiber FB2, are used as optical paths for guiding and transmitting various light beams including the emitted light beam La, the aiming light beam Le, the measuring light beam L1, the reference light beam L2, the return light beam L3 as described above, and the like, between the components, such as the respective optical devices.

The first light source 12 is configured to emit an OCT signal light beam (for example, a laser light beam having a wavelength of 1.3 µm or a low coherence light beam), and includes a light source 12a which emits the light beam La of either the laser light beam or the low coherence light beam, and a lens 12b which condenses the light beam La emitted from the light source 12a. As will be described in detail below, the light beam La emitted from the first light source 12 is made to pass through the optical fibers FB4 and FB3, so as to be divided into the measuring light beam L1 and the reference light beam L2 by the optical fiber coupler 14, and the measuring light beam L1 is inputted into the optical rotary adapter 18.

Further, the second light source 13 is configured to emit a visible colored light beam as the aiming light beam Le, in order to make a measured region easily recognized. It is possible to use, for example, a red semiconductor laser light beam having a wavelength of 0.66 µm, a helium-Ne laser light beam having a wavelength of 0.63 µm, a blue semiconductor laser light beam having a wavelength of 0.405 µm, and the like. Thus, the second light source 13 includes a semiconductor laser 13a which emits, for example, a red or blue or green laser light beam, and a lens 13b which condenses the aiming light beam Le emitted from the semiconductor laser 13a. The aiming light beam Le emitted from the second light source 13 is inputted into the optical rotary adapter 18 via the optical fiber FB8.

In the optical rotary adapter 18, the measuring light beam L1 and the aiming light beam Le are multiplexed with each other so as to be guided to the optical fiber FB1 in the optical probe 16. The multiplexing in the optical rotary adapter 18 will be described in detail below.

The optical fiber coupler (branching/multiplexing section) 14 is configured by, for example, a 2×2 optical fiber coupler, and is optically connected to each of the optical fiber FB2, the optical fiber FB3, the optical fiber FB5, and the optical fiber FB7.

The optical fiber coupler 14 divides the light beam La, which is made incident from the first light source 12 via the optical fibers FB4 and FB3, into the measuring light beam (first luminous flux) L1 and the reference light beam L2, so as to make the measuring light beam L1 incident on the optical fiber FB2, and to make the reference light beam L2 incident on the optical fiber FB5.

Further, the optical fiber coupler 14 multiplexes the light beam L2 which is made incident on the optical fiber FB5 and which is returned through the optical fiber FB5 after being subjected to a frequency shift and an optical path length adjustment by the optical path length adjusting section 26 as will be described below, with the light beam L3 which is acquired by the optical probe 16 as will be described below and which is guided from the optical fiber FB2. Also, the optical fiber coupler 14 emits the multiplexed light beam to the optical fiber FB3 (FB6) and the optical fiber FB7.

In the optical probe 16 which is connected with the optical fiber FB2 via the optical rotary adapter 18, the measuring light beam L1 multiplexed with the aiming light beam Le is made incident on the optical fiber FB1 from the optical fiber FB2 via the optical rotary adapter 18. The incident measuring light beam L1 multiplexed with the aiming light beam Le is transmitted by the optical fiber FB1, so as to be irradiated to the measuring object S. Then, the return light beam L3 from the measuring object S is acquired, and the acquired return light beam L3 is transmitted by the optical fiber FB1, so as to be emitted to the optical fiber FB2 via the optical rotary adapter 18.

The optical rotary adapter 18 is configured to rotatably connect the rotation side optical fiber FB1 to the fixed side optical fiber FB2, and also multiplexes the measuring light beam (first luminous flux) L1 with the aiming light beam (second luminous flux) Le. Note that the optical rotary adapter 18 will be described in detail below.

The interference light detecting section 20 is connected with the optical fiber FB6 and the optical fiber FB7, and is configured to detect, as interference signals, the interference light beams L4 and L5 which are generated by multiplexing the reference light beam L2 and the return light beam L3 in the optical fiber coupler 14.

Here, the optical tomographic imaging apparatus 10 includes the detector 30a which is provided on the optical path of the optical fiber FB6 branched from the optical fiber coupler 28 and which detects the light intensity of the laser light beam L4, and the detector 30b which is provided on the optical path of the optical fiber FB7 and which detects the light intensity of the interference light beam L5.

On the basis of the detection results of the detector 30a and the detector 30b, the interference light detecting section 20 adjusts the balance between the intensity of the interference light beam L4 detected from the optical fiber FB6, and the intensity of the interference light beam L5 detected from the optical fiber FB7.

The processing section 22 detects, from the interference signal detected by the interference light detecting section 20, a contact region between the optical probe 16 and the measuring object S at a measuring position, more precisely, a region in which the surface of the probe outer tube (described below) of the optical probe 16 is regarded as being in contact with the surface of the measuring object S, and further acquires a tomographic image from the interference signal detected by the interference light detecting section 20.

The display section 24 is configured by a CRT, a liquid crystal display apparatus, or the like, and displays the tomographic image transmitted from the processing section 22.

The optical path length adjusting section 26 is arranged on the side of the optical fiber FB5 on which side the reference light beam L2 is emitted (that is, at the end section of the optical fiber FB5 opposite to the optical fiber coupler 14).

The optical path length adjusting section 26 includes: a first optical lens 80 which converts the light beam emitted from the optical fiber FB5 into a parallel light beam; a second optical lens 82 which condenses the light beam made into the parallel light beam by the first optical lens 80; a reflection mirror 84 which reflects the light beam condensed by the second optical lens 82; a base 86 which supports the second optical lens 82 and the reflection mirror 84; and a mirror moving mechanism 88 which moves the base 86 in the direction in parallel with the optical axis direction, and adjusts the optical path length of the reference light beam L2 by changing the distance between the first optical lens 80 and the second optical lens 82.

The first optical lens 80 converts the reference light beam L2 emitted from the core of the optical fiber FB5 into a parallel light beam, and condenses the reference light beam L2 reflected by the reflection mirror 84 to the core of the optical fiber FB5.

Further, the second optical lens 82 condenses the reference light beam L2, which is converted into the parallel light beam by the first optical lens 80, on the reflection mirror 84, and converts the reference light beam L2 reflected by the reflection mirror 84 into the parallel light beam. In this way, a confocal optical system is formed by the first optical lens 80 and the second optical lens 82.

Further, the reflection mirror 84 is arranged at the focus of the light beam condensed by the second optical lens 82, and reflects the reference light beam L2 condensed by the second optical lens 82.

Thereby, the reference light beam L2 emitted from the optical fiber FB5 is converted into the parallel light beam by the first optical lens 80, and condensed on the reflection mirror 84 by the second optical lens 82. Thereafter, the reference light beam L2 reflected by the reflection mirror 84 is converted into the parallel light beam by the second optical lens 82, and condensed to the core of the optical fiber FB5 by the first optical lens 80.

Further, the second optical lens 82 and the reflection mirror 84 are fixed on the base 86, and the mirror moving mechanism 88 moves the base 86 in the optical axis direction (in the arrow A direction in FIG. 1) of the first optical lens 80.

By moving the base 86 in the arrow A direction by the mirror moving mechanism 88, it is possible to change the distance between the first optical lens 80 and the second optical lens 82, and possible to adjust the optical path length of the reference light beam L2.

The operation control section 32 includes an input device, such as a keyboard and a mouse, and a control device which manages various conditions on the basis of the inputted information, and is connected to the processing section 22 and the display section 24. On the basis of an operator's instruction inputted from the input device, the operation control section 32 performs the input, setting and change of various processing conditions, and the like, of the processing section 22, and the change, and the like, of the display settings of the display section 24.

Note that the operation control section 32 may be configured to display an operation screen in the display section 24, or may be configured to display an operation screen in a display section provided separately from the display section 24. Further, the operation control section 32 may also be configured to perform the operation control of the first light source 12, the second light source 13, the optical rotary adapter 18, the interference light detecting section 20, the optical path length, and the detecting sections 30a and 30b, and to perform the setting of various conditions.

Figure 2:
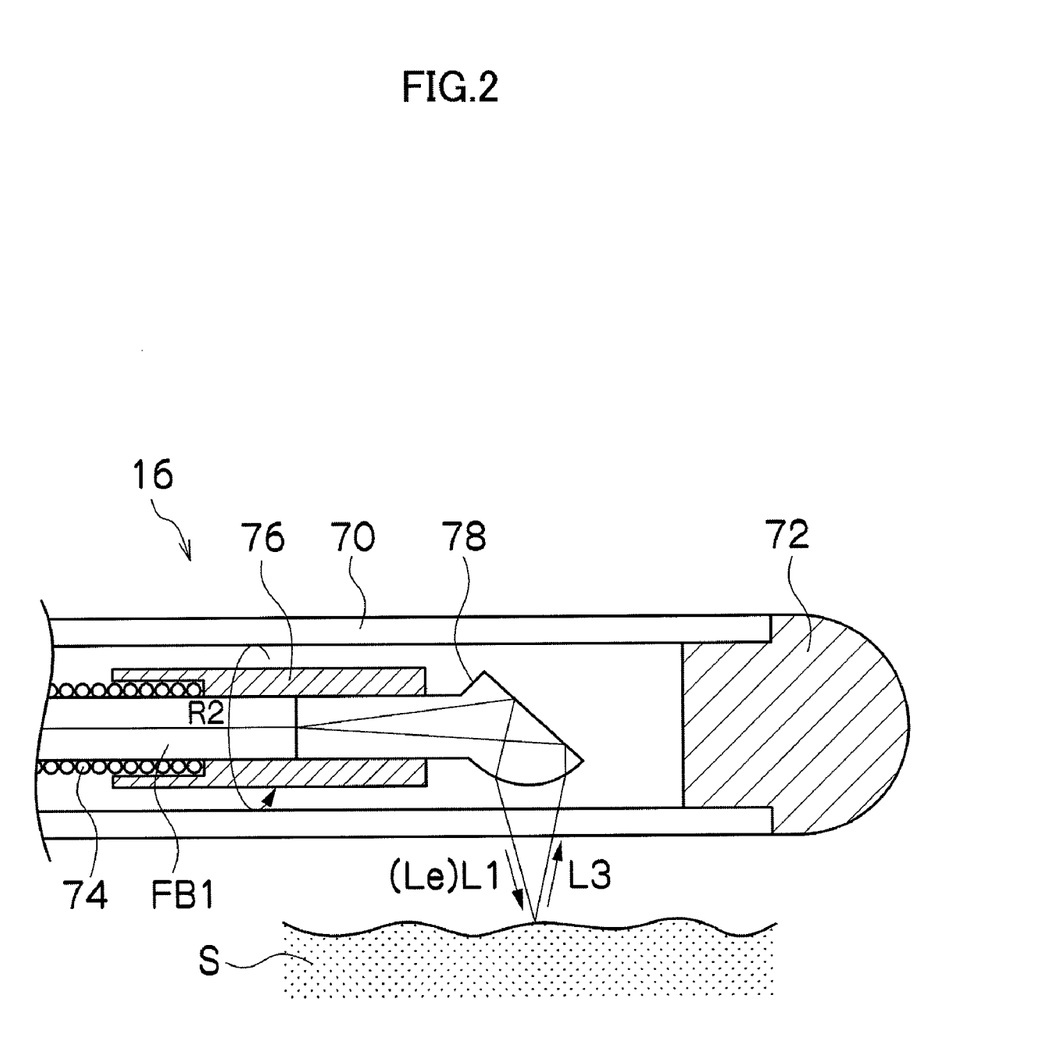
FIG. 2 is an enlarged partial sectional view showing a distal end section of an optical probe.

Next, the optical probe 16 will be described.

FIG. 2 is an enlarged partial sectional view showing a distal end section of the optical probe 16.

As shown in FIG. 2, the optical probe 16 according to the present embodiment includes a probe outer tube 70, a cap 72, the optical fiber FB1, a spring 74, a fixing member 76, and an optical lens 78.

The probe outer tube (sheath) 70 is a flexible cylindrical member, and is made of a material transmitting the measuring light beam Li multiplexed with the aiming light beam Le in the optical rotary adapter 18, and the return light beam L3. Note that in the probe outer tube 70, only a part on the side of the distal end (which is the distal end of the optical fiber FB1 on the side opposite to the optical rotary adapter 18, and is hereinafter referred to as the distal end of the probe outer tube 70) through which part the measuring light beam L1 (aiming light beam Le) and the return light beam L3 are made to pass, may be formed of a light transmitting material (transparent material) over the entire periphery thereof.

The cap 72 is formed at the distal end of the probe outer tube 70, and closes the distal end of the probe outer tube 70.

The optical fiber FB1 is a linear member and is housed in the probe outer tube 70 along the probe outer tube 70. The optical fiber FB1 guides, to the optical lens 78, the measuring light beam L1 which is emitted from the optical fiber FB2 and which is multiplexed, in the optical rotary adapter 18, with the aiming light beam Le emitted from the optical fiber FB8. Also, the optical fiber FB1 guides the return light beam L3 from the measuring object S, which return light beam is acquired through the optical lens 78 by irradiating the measuring object S with the measuring light beam L1 (aiming light beam Le), to the optical rotary adapter 18, so as to make the return light beam L3 incident on the optical fiber FB2.

Here, the optical fiber FB1 and the optical fiber FB2 are optically connected to each other by the optical rotary adapter 18, in the state where the rotation of the optical fiber FB1 is not transmitted to the optical fiber FB2. Further, the optical fiber FB1 is arranged rotatably with respect to the probe outer tube 70.

The spring 74 is fixed to the outer periphery of the optical fiber FB1. Further, the optical fiber FB1 and the spring 74 are connected to the optical rotary adapter 18.

The optical lens 78 is arranged at the measurement side distal end of the optical fiber FB1 (the distal end of the optical fiber FB1 on the side opposite to the optical rotary adapter 18), and the distal end section of the optical lens 78 is formed in an approximately spherical shape so that the measuring light beam L1 (aiming light beam Le) emitted from the optical fiber FB1 is condensed to the measuring object S.

The optical lens 78 irradiates the measuring object S with the measuring light beam L1 (aiming light beam Le) emitted from the optical fiber FB1, and condenses the return light beam L3 from the measuring object S so as to make the return light beam L3 incident on the optical fiber FB1.

The fixing member 76 is arranged at the outer periphery of the connecting section of the optical fiber FB1 and the optical lens 78, so as to fix the optical lens 78 to the end section of the optical fiber FB1. Here, the method of fixing the optical fiber FB1 to the optical lens 78 by the fixing member 76 is not limited in particular. The optical fiber FB1 and the optical lens 78 may be stuck and fixed to the fixing member 76 by an adhesive, or may also be fixed to the fixing member 76 by a mechanical structure using a bolt, and the like. Note that as the fixing member 76, any member may be used as long as the member is included in those, such as a zirconia ferrule and a metal ferrule, which are used for fixation, holding or protection of an optical fiber.

Further, the optical fiber FB1 and the spring 74 are connected to a rotary cylinder (described below) of the optical rotary adapter 18. Thus, it is possible to rotate the optical lens 78 with respect to the probe outer tube 70 in the arrow R2 direction by rotating the optical fiber FB1 and the spring 74 with the rotary cylinder. Further, the optical rotary adapter 18 includes a rotary encoder, and detects the irradiation position of the measuring light beam L1 from the positional information (angle information) on the optical lens 78 on the basis of the signal from the rotary encoder. That is, the optical rotary adapter 18 detects a measuring position by detecting an angle with respect to the reference position in the rotation direction of the rotating optical lens 78.

In the optical probe 16 which is configured as described above, the optical fiber FB1 and the spring 74 are rotated by the optical rotary adapter 18 in the arrow R2 direction in FIG. 2. Thereby, the optical probe 16 irradiates the measuring object S with the measuring light beam L1 (aiming light beam Le) emitted from the optical lens 78 to acquire the return light beam L3, while scanning the measuring light beam L1 in the arrow R2 direction (in the circumferential direction of the probe outer tube 70). The aiming light beam Le is irradiated to the measuring object S as a spot light beam of, for example, blue, red, or green. The reflected light beam of the aiming light beam Le is also displayed as a luminescent spot on the observed image displayed in the display section 24.

Thereby, it is possible to accurately capture a desired region of the measuring object S over the entire circumference in the circumferential direction of the probe outer tube 70, and also, it is possible to acquire the return light beam L3 reflected from the measuring object S.

Figure 3:
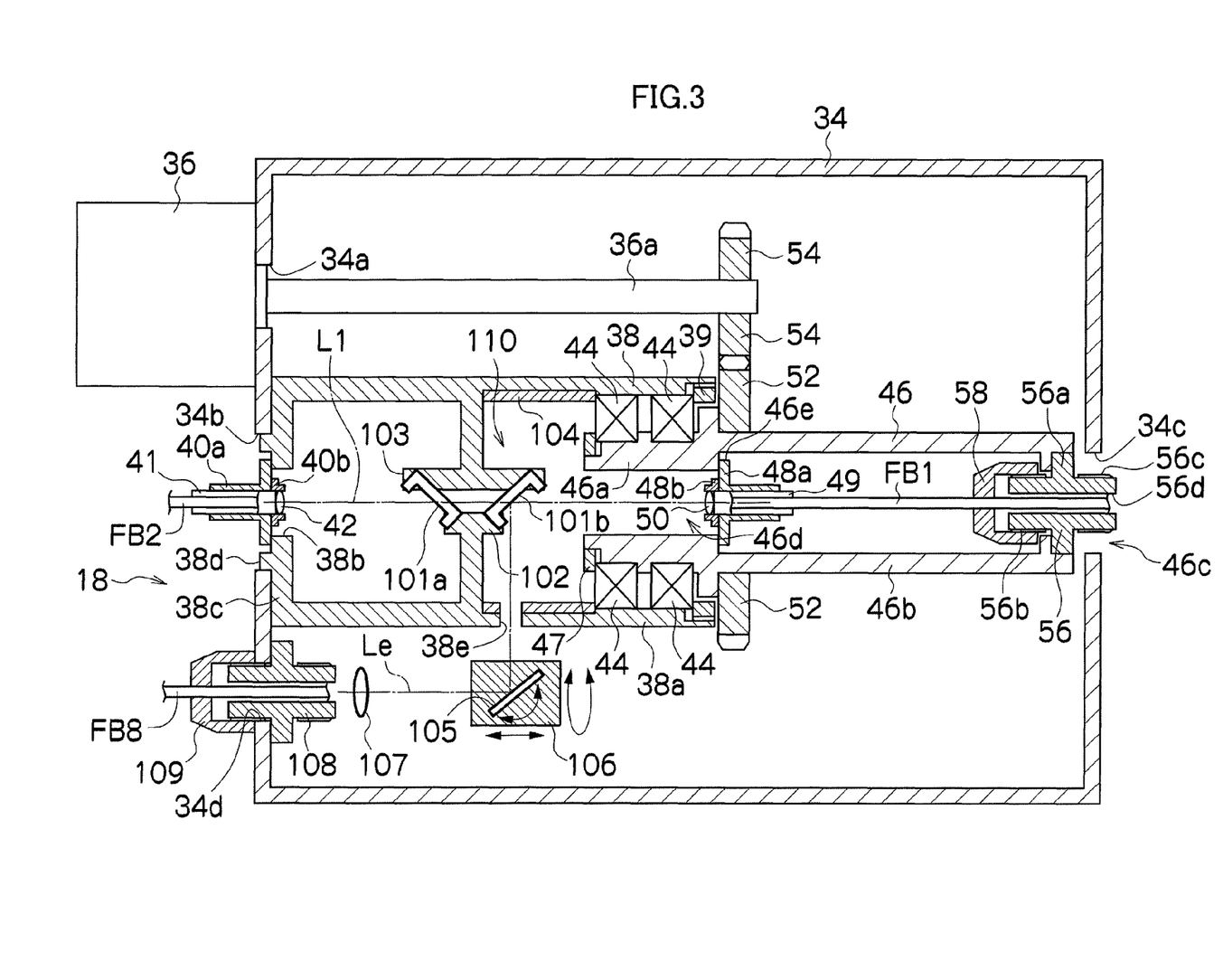
FIG. 3 is a schematic sectional view of the optical rotary adapter according to the first embodiment of the present invention.

Next, there will be described the optical rotary adapter 18 according to the present invention.

FIG. 3 is a schematic sectional view of the optical rotary adapter according to the first embodiment of the present invention.

As shown in FIG. 3, the optical rotary adapter 18 includes: a case 34; a motor 36 attached to the outside of the case 34; a fixed sleeve 38 fixed in the case 34; the fixed side optical fiber FB2 and a fixed side collimator lens 42 which are attached via holders 40a and 40b fixedly attached to the fixed sleeve 38; a rotary cylinder 46 rotatably supported by the fixed sleeve 38 via bearings 44; the rotation side optical fiber FB1 and a rotation side collimator lens 50 which are attached via holders 48a and 48b fixedly attached substantially at the center of the rotary cylinder 46; a gear 52 attached to the outer periphery of the rotary cylinder 46; and a gear 54 which is attached to a rotary shaft 36a of the motor 36, and which is in mesh with the gear 52 of the rotary cylinder 46.

The case 34 is configured to house the respective components of the optical rotary adapter 18, except for the motor 36, the holder 40a, the fixed side optical fiber FB2, and the like. In the case 34, there is provided an opening 34a into which the rotary shaft 36a of the motor 36 is inserted. Further, in the case 34, there are provided, at positions facing each other, an opening 34b for attaching the fixed sleeve 38 to which the holder 40a for holding the optical fiber FB2 is attached, and an opening 34c for allowing the optical fiber FB1 to rotatably pass therethrough. Further, in the case 34, there is provided an opening 34d for attaching holders 108 and 109 which are used to hold the optical fiber FB8 for guiding the aiming light beam Le.

The motor 36 is provided to rotate the optical fiber FB1 supported substantially at the center of the rotary cylinder 46 by rotating the rotary cylinder 46. The motor 36 rotates the rotary shaft 36a thereof to thereby rotate the gear 54 attached at the distal end of the rotary shaft 36a. Thereby, the gear 52 of the rotary cylinder 46 which gear is in mesh with the gear 54 is rotated, so as to rotate the rotary cylinder 46. As a result, the optical fiber FB1 supported substantially at the center of the rotary cylinder 46 is rotated.

The fixed sleeve 38 is configured to support the fixed side optical fiber FB2 and the fixed side collimator lens 42 at predetermined positions, and is also configured to rotatably support the rotary cylinder 46. The fixed sleeve 38 is formed in a cylindrical shape, and includes a circular tube section 38a opened on one side thereof and a disk section 38c having a center opening 38b on the other side. The disk section 38c is attached to the inner wall of the case 34 so that an annular projection 38d outside the disk section 38c is fitted to the opening 34b of the case 34.

In this way, to the outside of the disk section 38c of the fixed sleeve 38 fixed to the case 34, the flange section of the holder 40a is attached so that the flange section covers the center opening 38b.

On the other hand, a distal end section 46a of the rotary cylinder 46 is fitted into the circular tube section 38a of the fixed sleeve 38 from the opening side, and the two bearings 44 are provided between the inner periphery of the circular tube section 38a of the fixed sleeve 38 and the outer periphery of the cylindrical distal end section 46a of the rotary cylinder 46. The two bearings 44 are pressed against the step section of the inner periphery of the circular tube section 38a of the fixed sleeve 38, and are fixed by a ring 39 having a male screw section which is screwed into the female screw section formed on the inner peripheral surface at the open end of the circular tube section 38a, so as to be prevented from coming off from the inner periphery of the circular tube section 38a to the open side.

The holder 40a is a flanged circular tube member for holding, at the center thereof, the optical fiber FB2 held by a cylindrical ferrule 41. The optical fiber FB2 held by the ferrule 41 is held by the holder 40a so that the distal end surface of the optical fiber FB2 is positioned at a predetermined distance away from the flange side end surface of the holder 40a.

Here, the ferrule 41 has a core section with the optical fiber FB2 inserted therein and has a function to hold and protect the optical fiber FB2. Usually, it is possible to use, as the ferrule 41, a zirconia ferrule, a metal ferrule using a metal, such as a nickel alloy, and the like.

On the other hand, the holder 40b is a flanged circular tube member for holding the collimator lens 42. The flange section of the holder 40b is attached to the flange section of the holder 40a so that the distal end center of the optical fiber FB2 is separated from the center of collimator lens 42 along the optical axis by a predetermined distance, specifically, by the focal distance of the collimator lens 42.

The fixed side optical fiber FB2 transmits the measuring light beam L1 branched by the optical fiber coupler 14 to the rotation side optical fiber FB1, and transmits the return light beam L3 guided by the optical fiber FB1. The distal end surface of the optical fiber FB2 and the distal end surface of the ferrule 41 having the core section with the optical fiber FB2 inserted therein are formed as inclined end surfaces located on the same plane which is inclined at a predetermined angle with respect to the plane perpendicular to the optical axis of the optical fiber FB2.

The fixed side collimator lens 42 collimates the measuring light beam L1 emitted from the distal end of the optical fiber FB2, so as to make the measuring light beam L1 incident on the rotation side collimator lens 50, and condenses the collimated return light beam L3 from the collimator lens 50, so as to make the return light beam L3 incident on the optical fiber FB2. The distal end surface of the optical fiber FB2 and the collimator lens 42 are arranged so that the distance (on the optical axis) between the center of the inclined end surface of the optical fiber FB2 and the center of the collimator lens 42 is equal to the focal distance of the collimator lens 42.

The rotary cylinder 46 is a member, the distal end section 46a of which is fitted into the circular tube section 38a of the fixed sleeve 38 so as to be rotatably supported by the fixed sleeve 38 via the two bearings 44, and which rotates the rotation side optical fiber FB1 while holding the optical fiber FB1 substantially at the inner center thereof.

The rotary cylinder 46 includes: the cylindrical distal end section 46a, the distal end of which faces the disk section 38c of the fixed sleeve 38, on the outer peripheral section of which the two bearings 44 are arranged, and at the rear end of which the optical fiber FB1 is attached; a circular tube section 46b having an inner peripheral surface which is connected to the distal end section 46a and which has an inner diameter larger than that of the distal end section 46a; and a connecting section 46c which is connected to the circular tube section 46b and which is used to connect the optical fiber FB1 in the inside thereof to the optical fiber FB1 in the optical probe 16.

The two bearings 44 are pressed against the step section on the outer periphery of the distal end section 46a of the rotary cylinder 46, and are fixed by a ring 47 having a female screw section into which a male screw section formed on the outer peripheral surface at the open end of the distal end section 46a is screwed so that the two bearings 44 are prevented from coming off from the outer periphery of the distal end section 46a to the open side.

Further, on the outer periphery of the rotary cylinder 46, a flange-like step section is provided between the distal end section 46a and the circular tube section 46b, and the gear 52 is attached to the outer periphery of the rotary cylinder 46 by being pressed against the step section.

The flange section of the holder 48a is attached to the rear end 46d of the distal end section 46a which is connected to the diameter enlarged circular tube section 46b of the rotary cylinder 46, so as to cover the center opening 46e of the rear end 46d.

The holder 48a is, similarly to the holder 40a, a flanged circular tube member for holding, at the center thereof, the optical fiber FB1 held by a cylindrical ferrule 49. The optical fiber FB1 held by the ferrule 49 is held by the holder 48a so that the distal end surface of the optical fiber FB1 is positioned at a predetermined distance away from the flange side end surface of the holder 48a.

Here, the ferrule 49 has a core section with the optical fiber FB1 inserted therein and has a function to hold and protect the optical fiber FB1. Usually, similarly to the ferrule 41, it is possible to use, as the ferrule 49, a zirconia ferrule, a metal ferrule using a metal, such as a nickel alloy, and the like.

On the other hand, the holder 48b is, similarly to the holder 40b, a flanged circular tube member for holding the collimator lens 50. The flange section of the holder 48b is attached to the flange section of the holder 48a so that the distal end center of the optical fiber FB1 is separated from the center of collimator lens 50 along the optical axis by a predetermined distance, specifically, by the focal distance of the collimator lens 50.

The rotation side optical fiber FB1 is configured to guide the measuring light beam L1, which is transmitted from the fixed side optical fiber FB2 and which is multiplexed with the aiming light beam Le transmitted from the optical fiber FB8 as will be described below, to the measuring object S, and is configured to guide the return light beam L3 from the measuring object S to transmit the return light beam L3 to the fixed side optical fiber FB2. The distal end surface of the optical fiber FB1 and the distal end surface of the ferrule 49 having the core section with the optical fiber FB1 inserted therein are formed as inclined end surfaces located on the same plane which is inclined at a predetermined angle with respect to the plane perpendicular to the optical axis of the optical fiber FB1.

The rotation side collimator lens 50 condenses the collimated measuring light beam L1 from the collimator lens 42, so as to make the measuring light beam L1 incident on the optical fiber FB1, and collimates the return light beam L3 emitted from the distal end of the optical fiber FB1, to make the return light beam L3 incident on the fixed side collimator lens 42. The distal end surface of the optical fiber FB1 and the collimator lens 50 are arranged so that the distance (on the optical axis) between the center of the inclined end surface of the optical fiber FB1 and the center of the collimator lens 50 is equal to the focal distance of the collimator lens 50.

The connecting section 46c of the rotary cylinder 46 includes: an end surface member 56 having a flange section 56a which is fitted into the other open end of the circular tube section 46b and which is brought into contact with the step section provided on the inner periphery of the other open end, male screw sections 56b and 56c provided on both sides of the flange section 56a, and a central through hole 56d into which there is inserted the optical fiber FB1 held substantially at the center of the rotary cylinder 46 by the holder 48a via the ferrule 49; and a cap 58 which has a center opening with the optical fiber FB1 inserted therein and a female screw section screwed to the male screw section 56b, and which holds the optical fiber FB1 inserted into the central through hole 56d.

Here, the male screw section 56c of the connecting section 46c of the rotary cylinder 46 faces the opening 34c of the case 34, and functions as a connector of the optical fiber FB1 of the optical probe 16, so as to be able to be connected with an optical connecter, such as an SC connector and an FC connector for ordinary physical contact. Similarly, the optical fibers FB2 and FB3 can also be connected via optical connecters. Note that as will be described below, the optical fiber FB1 is covered by a spring, or the like, in order to be held and protected in the optical probe 16 in a state of having a certain degree of flexibility.

In the optical rotary adapter 18 according to the present invention, for example, by removing the ring 39, it is also possible to extract and remove the rotary cylinder 46 to which the holder 48a holding the optical fiber FB1 is kept attached, from the fixed sleeve 38 to which the holder 40a holding the optical fiber FB2 is kept attached. In this case, the rotary cylinder 46 is extracted from the inner periphery of the fixed sleeve 38 together with the two bearings 44 or with the distal end section 46a of the rotary cylinder 46.

At this time, since the collimator lenses 50 and 42 are attached at the distal end of the optical fibers FB1 and FB2, it is possible to prevent the distal end of the optical fibers FB1 and FB2 from being accidentally damaged or broken.

Note that in the illustrated example, the connecting section 46c of the rotary cylinder 46 is configured so as to function as a connector of the optical fiber, but can also be configured to hold the optical fiber FB1 held by the holder 48a in the rotary cylinder 46 so that the held optical fiber FB1 is extended to the distal end of the optical probe 16 as it is.

Next, there will be described the multiplexing device according to the present invention.

As shown in FIG. 3, a multiplexing device 110 is provided between the fixed side collimator lens 42 and the rotation side collimator lens 50. The multiplexing device 110 is configured by an optical-axis compensating plate 101a, a dichroic mirror 101b, and a reflection mirror 105 which reflects the aiming light beam Le emitted from the optical fiber FB8 so as to make the aiming light beam Le incident on the dichroic mirror 101b.

The dichroic mirror 101b has a transmission characteristic for the OCT signal light beam (having, for example, a wavelength of 1.3 μm) and has a reflection characteristic for the aiming light beam (having, for example, a visible light wavelength of 0.65 μm). Further, the optical-axis compensating plate 101a is used to correct an optical axis shift which is caused because if only the dichroic mirror 101b is provided, the optical axis of the measuring light beam L1 (OCT signal light beam) emitted from the optical fiber FB2 is shifted due to the thickness of dichroic mirror 101b before and after the measuring light beam L1 is transmitted through the dichroic mirror 101b. The optical-axis compensating plate 101a is arranged to face the dichroic mirror 101b at an angle of 90° therebetween.

The dichroic mirror 101b and the optical-axis compensating plate 101a are fixed in a parallel light beam forming section in the fixed sleeve 38 by a mirror holder 102 and a mirror fixing ring 103 and by a housing fixing ring 104. The housing fixing ring 104 is fixed to the circular tube section 38a of the fixed sleeve 38 by the bearing 44 and the ring (bearing fixing screw) 39.

The measuring light beam L1 emitted from the optical fiber FB2 is formed into a parallel light beam by the fixed side collimator lens 42, so as to be made incident on the dichroic mirror 101b. At this time, the measuring light beam L1, to which an optical axis shift (opposite to the optical axis shift caused by the dichroic mirror 101b) is given beforehand by the optical-axis compensating plate 101a, is made incident on the dichroic mirror 101b and transmitted through the dichroic mirror 101b so as to be emitted on the original optical axis.

On the other hand, in front of the optical fiber FB8 which emits the aiming light beam Le, there is arranged a collimator lens 107 by a fixing member (not shown), and there is provided a mirror adjusting mechanism 106 which adjusts the position of reflection mirror 105 for reflecting the aiming light beam Le to the dichroic mirror 101b. Further, there is provided an opening 38e for guiding the aiming light beam Le reflected by the reflection mirror 105 to the dichroic mirror 101b in the fixed sleeve 38.

The aiming light beam Le emitted from the optical fiber FB8 is formed into a parallel light beam by the collimator lens 107, and is made incident on the dichroic mirror 101b by the reflection mirror 105. At this time, the reflection mirror 105 can be adjusted by being swung, oscillated and parallelly moved by the mirror adjusting mechanism 106 as shown by the arrows in the figure.

Thereby, the aiming light beam Le is multiplexed with the measuring light beam L1 made incident on the dichroic mirror 101b from the side of the fixed side collimator lens 42 on the same axis on the surface of the dichroic mirror 101b. The measuring light beam L1 multiplexed with the aiming light beam Le is guided to the rotatable optical fiber FB1 by the rotation side collimator lens 50.

In the following, there will be described operations of the optical tomographic imaging apparatus 10 and the optical rotary adapter 18 according to the present embodiment.

First, by moving the base 86 in the arrow A direction by the mirror moving mechanism 88 of the optical path length adjusting section 26 shown in FIG. 1, the optical path length is adjusted and set so that the measuring object S is positioned within the measurable region.

Thereafter, the laser light beam La is emitted from the first light source 12, and the aiming light beam Le is emitted from the second light source 13. The emitted laser light beam La is divided into the measuring light beam L1 and the reference light beam L2 by the optical fiber coupler (branching/multiplexing section) 14. The measuring light beam L1 is guided to the optical rotary adapter 18 from the optical fiber FB2. On the other hand, the emitted aiming light beam Le is also guided to the optical rotary adapter 18 from the optical fiber FB8.

The measuring light beam L1 is multiplexed with the aiming light beam Le in the optical rotary adapter 18. The aiming light beam Le and the measuring light beam L1, which are multiplexed with each other, are guided to the optical probe 16 by the optical fiber FB1, so as to be irradiated to the measuring object S. The aiming light beam Le can be visually recognized and hence serves as a measuring mark.

At this time, the optical fiber FB1 and the optical lens 78 in the optical probe 16 are rotated by the optical rotary adapter 18. That is, in the optical rotary adapter 18, the motor 36 is driven and the rotary shaft 36a is rotated. Thereby, the gear 54 attached at the distal end of the rotary shaft 36a is rotated and the gear 52 in mesh with the gear 54 is rotated. The rotary cylinder 46 rotatably supported by the fixed sleeve 38 via the bearings 44 is rotated by the rotation of the gear 52, so that the optical fiber FB1 held by the holder 48a, and the like, substantially at the center of the rotary cylinder 46 is rotated.

Note that the optical fiber FB1 held in the rotary cylinder 46 is connected to the optical fiber FB1 in the optical probe 16 at the connecting section 46c of the rotary cylinder 46 or is extended to the optical probe 16 through the connecting section 46c of the rotary cylinder 46, and hence the optical fiber FB1 in the optical probe 16 and the optical lens 78 attached at the distal end of the optical fiber FB1 are also rotated by the rotation of optical fiber FB1 in the rotary cylinder 46.

On the other hand, the measuring light beam L1, which is optically transmitted by the optical fiber FB2 held by the holder 40a of the fixed sleeve 38 and which is emitted from the inclined end surface of the optical fiber FB2, is made incident on the collimator lens 42 held by the holder 40b of the fixed sleeve 38, so as to be collimated, and is then made incident on the collimator lens 50 held by the holder 48b in the rotating rotary cylinder 46, so as to be condensed. Thereafter, the measuring light beam L1 is made incident on the inclined end surface of the optical fiber FB1 held by the holder 48a in the rotary cylinder 46, so as to be optically transmitted into the optical fiber FB1 in the optical probe 16. Further, the measuring light beam L1 is made incident on the optical lens 78, and is transmitted through the probe outer tube 70 from the optical lens 78, so as to be irradiated to the measuring object S.

At this time, the optical fiber FB1 and the optical lens 78 in the optical probe 16 are rotated by the optical rotary adapter 18, and hence the measuring light beam L1 is irradiated to the measuring object S, such as a body cavity, over the entire periphery thereof by the rotating optical lens 78. At this time, the aiming light beam Le is also irradiated, so that the measuring position can be visually confirmed by the luminescent spot displayed in the display section 24. Further, as the precise position, the information on the measuring position of the measuring object S can be detected by the rotary encoder (not shown), and the like, provided in the optical rotary adapter 18.

Then, the light beam reflected at each depth position of the measuring object S is made incident on the optical probe 16 as the return light beam L3. Also at this time, the optical fiber FB1 and the optical lens 78 in the optical probe 16 are rotated by the optical rotary adapter 18, and hence the return light beam L3 from the entire periphery of the measuring object S is made incident on the rotating optical lens 78. The return light beam L3 is made incident on the optical fiber coupler 14 via the optical probe 16 (optical fiber FBI), the optical rotary adapter 18, and the optical fiber FB2.

Here, the return light beam L3 from the measuring object S is transmitted through the probe outer tube 70 of the optical probe 16, so as to be made incident on the rotating optical lens 78, and is then optically transmitted into the optical fiber FB1 in the optical probe 16 from the optical lens 78, so as to be made incident on the optical fiber FB1 held by the holder 48a in the rotary cylinder 46 of the optical rotary adapter 18. In the optical rotary adapter 18, the return light beam L3 emitted from the inclined end surface of the rotating optical fiber FB1 is made incident on the rotation side collimator lens 50 held by the holder 48b in the rotating rotary cylinder 46, so as to be collimated. Thereafter, the return light beam L3 is made incident on the fixed side collimator lens 42 held by the holder 40b of the still fixed sleeve 38, so as to be condensed. Then, the return light beam L3 is made incident on the inclined end surface of the optical fiber FB2 held by the holder 40a of the fixed sleeve 38, and is optically transmitted through the optical fiber FB2, so as to be made incident on the optical fiber coupler 14.

On the other hand, the reference light beam L2 is made incident on the optical path length adjusting section 26 via the optical fiber FB5. Then, the reference light beam L2, the optical path length of which is adjusted by the optical path length adjusting section 26, is again guided by the optical fiber FB5, so as to be made incident on the optical fiber coupler 14.

Then, in the optical fiber coupler 14, the return light beam L3 from the measuring object S is multiplexed with the reference light beam L2, the optical path length of which is adjusted by the optical path length adjusting section 26. The interference light beams L4 and L5 of the return light beam L3 and the reference light beam L2 are generated. The interference light beam is detected by the interference light detecting section 20 as an interference signal. The detected interference signal is sent to the processing section 22. In the processing section 22, when the sent interference signal is acquired, the information on the measuring position detected by the optical rotary adapter 18 is acquired, so that the interference signal is made to correspond to the positional information on the measuring position.

In the processing section 22, the contact region between the probe outer tube 70 and the measuring object S is detected, so that a tomographic image in the depth direction in the contact region is generated. Then, the tomographic image subjected to the image quality correction processing is displayed in the display section 24.

In this way, in the present embodiment, the aiming light beam is multiplexed by utilizing the function which prevents the regularly reflected light from being returned while improving the S/N by reducing unnecessary reflected light in the OCT optical rotary adapter section. Thereby, it is possible to avoid the loss of the OCT signal light beam which loss is caused in the aiming light multiplexing function section incorporated in the conventional optical fiber interferometer, and also it is possible to improve the visibility of the portion subjected to the OCT measurement.

Note that in the present embodiment, the same mirror as the dichroic mirror 101b is arranged so as to face the dichroic mirror 101b at the angle of 90° thereto, and is used as the optical-axis compensating plate 101a. However, the device which compensates the optical axis shift so as to prevent the optical axis of the luminous flux after the multiplexing from being shifted from the optical axis of the first luminous flux (measuring light beam L1) before the multiplexing, is not limited to this.

For example, in order that the optical axis of the luminous flux transmitted through the dichroic mirror 101b is made to coincide with the center of the rotation side collimator lens 50 and of the rotation side optical fiber FB1, the fixed side optical fiber FB2 and the fixed side collimator lens 42 may be arranged to be shifted so that the optical axis of the luminous flux made incident on the dichroic mirror 101b is shifted beforehand to cancel the shift of the optical axis caused by the dichroic mirror 101b.

Figure 4:
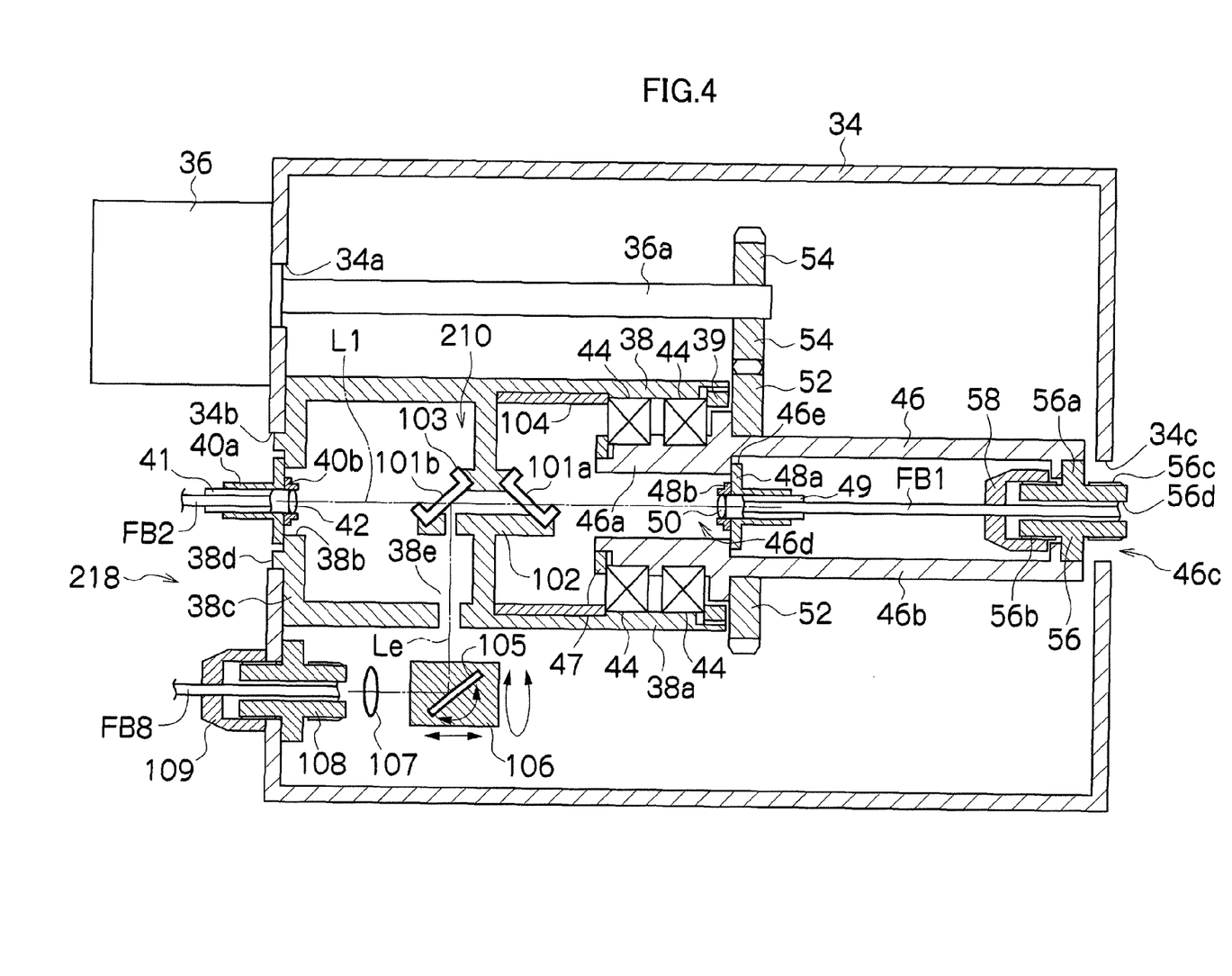
FIG. 4 is a schematic sectional view of an optical rotary adapter according to a second embodiment.

Next, there will be described an optical rotary adapter according to a second embodiment of the present invention.

FIG. 4 is a schematic sectional view of an optical rotary adapter according to the second embodiment.

As shown in FIG. 4, an optical rotary adapter 218 according to the second embodiment is configured such that the positions of the dichroic mirror 101b and the optical-axis compensating plate 101a of the multiplexing device 110 in the optical rotary adapter 18 of the above described first embodiment are replaced in the light traveling direction and their arrangement is reversed.

That is, in a multiplexing device 210 arranged in the parallel light beam forming section in the fixed sleeve 38 of the present embodiment, the dichroic mirror 101b is arranged on the side nearer to the fixed side collimator lens 42, and the optical-axis compensating plate 101a is arranged on the side nearer to the rotation side collimator lens 50. Further, the dichroic mirror 101b and the optical-axis compensating plate 101a are arranged to face each other at an angle of 90° therebetween.

Further, the position of the reflection mirror 105 for making the aiming light beam Le incident on the dichroic mirror 101b, and the position of the opening 38e which is provided in the fixed sleeve 38 in order to secure an optical path to enable the reflected light from the reflection mirror 105 to reach the dichroic mirror 101b, are also changed in correspondence with the reversed arrangement.

Note that the configuration other than the change in the mirror arrangement configuring the multiplexing device 210 is the same as that of the above described first embodiment.

Even when the arrangement of the dichroic mirror 101b and the optical-axis compensating plate 101a is reversed in this way, it is possible to obtain the same effect as the above described first embodiment.

Figure 5:
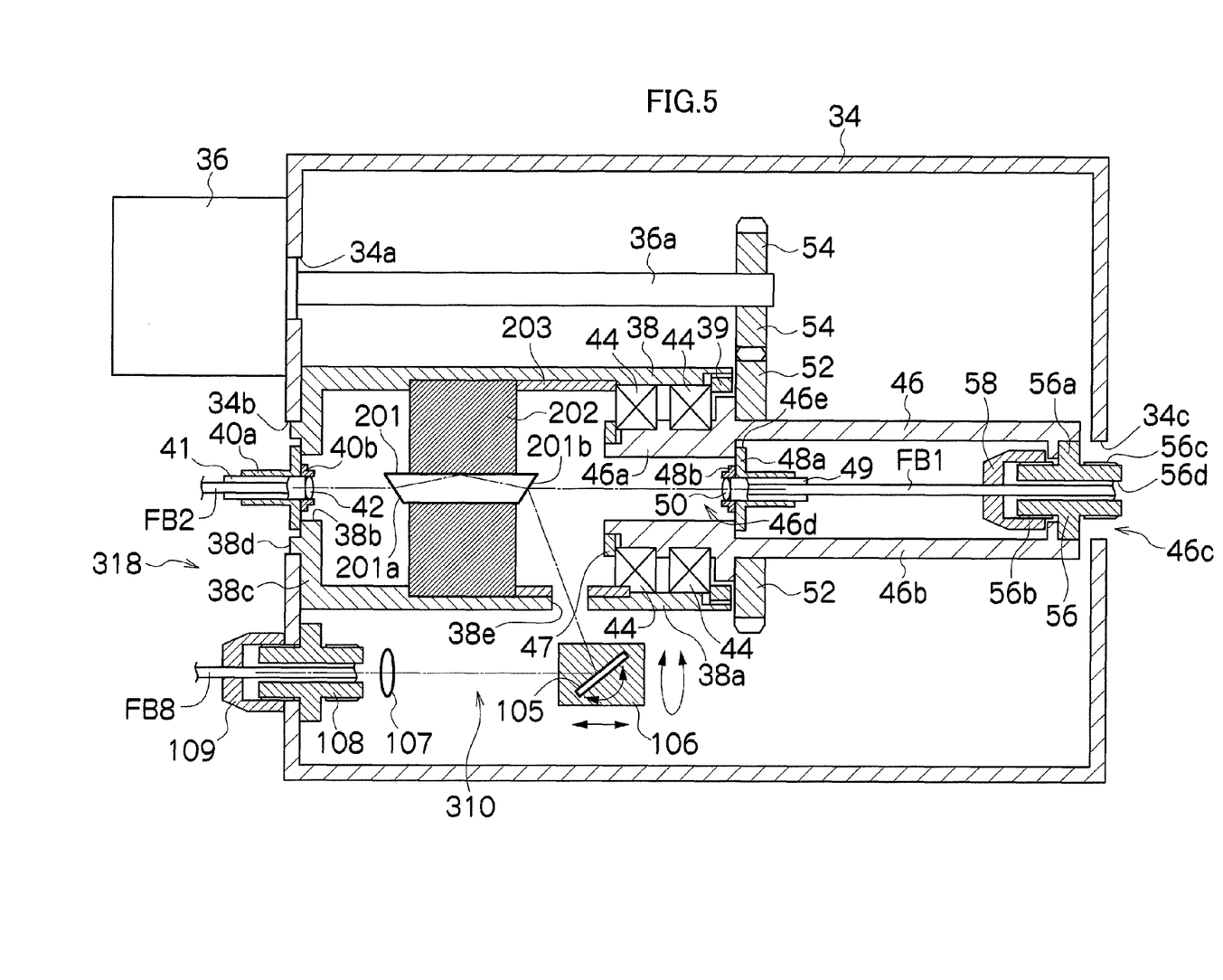
FIG. 5 is a schematic sectional view of an optical rotary adapter according to a third embodiment.

Next, there will be described a third embodiment according to the present invention.

FIG. 5 is a schematic sectional view showing an optical rotary adapter according to the third embodiment.

As shown in FIG. 5, in an optical rotary adapter 318 of the third embodiment, a multiplexing device 310 is configured by using a trapezoidal prism 201 having two surfaces which face each other and are inclined at respective angles having the same magnitude in the opposite directions, instead of the dichroic mirror 101b and the optical-axis compensating plate 101a of the multiplexing device 110 in the optical rotary adapter 18 according to the above described first embodiment.

The trapezoidal prism 201 is fixed in the fixed sleeve 38 by a prism holder 202 and a prism fixing ring 203. The two oppositely facing surfaces 201a and 201b positioned in the light traveling direction of the trapezoidal prism 201 are respectively formed at angles having the same magnitude in the opposite directions. The measuring light beam L1, which is emitted from the fixed side optical fiber FB2 and which is converted into the parallel luminous flux via the fixed side collimator lens 42, is made incident on the surface 201a of the trapezoidal prism 201. Thereafter, the measuring light beam L1 is reflected in the trapezoidal prism 201, and is then emitted from the surface 201b.

The measuring light beam L1 and the aiming light beam Le are multiplexed in such a manner that the aiming light beam Le, which is emitted from the optical fiber FB8 and which is converted into a parallel light beam by the collimator lens 107, is reflected by the reflection mirror 105 to be made incident on the surface 201b of the trapezoidal prism 201.

At this time, the reflection mirror 105 is adjusted by being swung, oscillated and parallelly moved by the mirror adjustment mechanism 106 so that the aiming light beam Le is multiplexed with the measuring light beam L1 on the same axis on the surface 201b of the trapezoidal prism 201. Further, the opening 38e, which is provided in the fixed sleeve 38 and which serves as the optical path of the aiming light beam Le, is also formed a little larger in diameter in this case.

Also in the present embodiment, the configuration other than the multiplexing device 310 is the same as that of the above described first embodiment. Also in the present embodiment, it is possible to obtain the same effect as that of the first and second embodiments.

Figure 6:
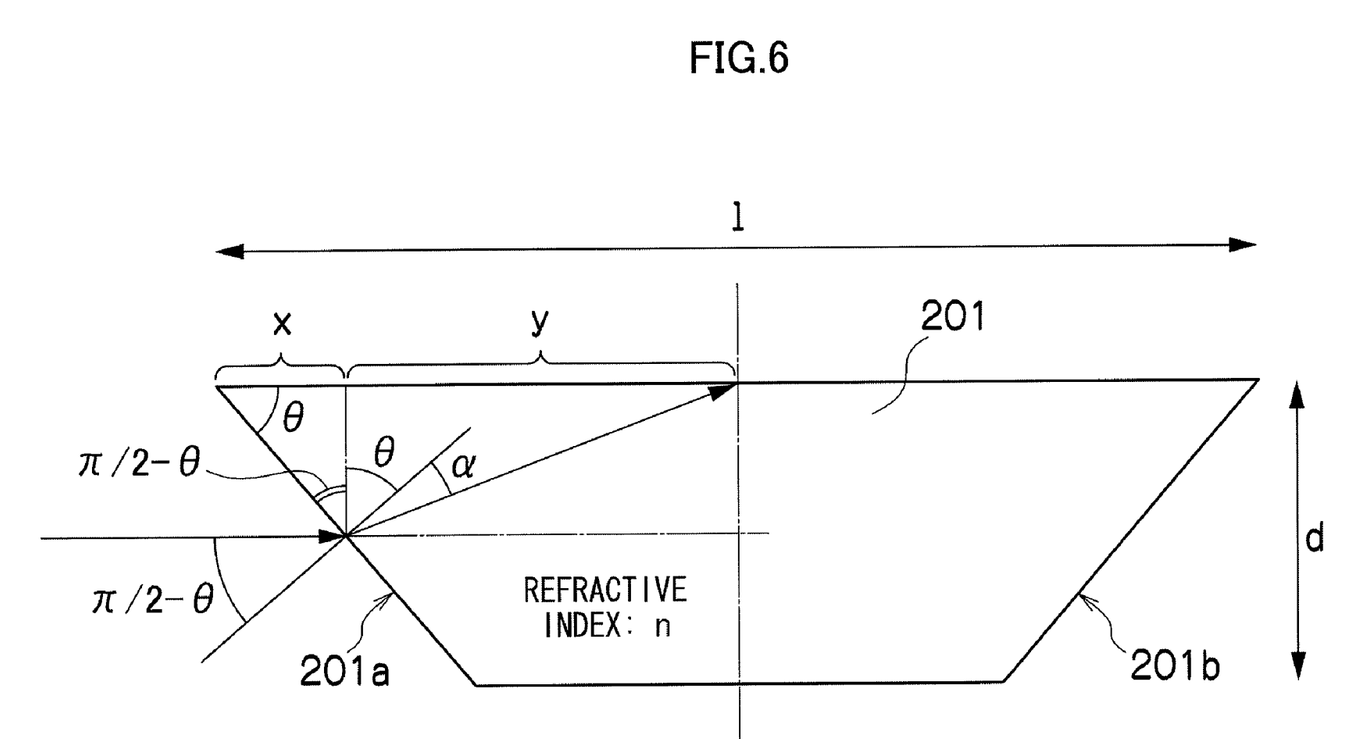
FIG. 6 is an enlarged sectional view showing the prism in FIG. 5.

In the following, there will be described specific dimensional conditions of the prism 201.

FIG. 6 is an enlarged sectional view showing the prism 201. As shown in FIG. 6, the prism 201 has two inclined surfaces 201a and 201b which face each other at respective angles having the same magnitude θ in the opposite directions.

When the refractive index of the prism 201 is set to n, and when the angle between the refracted light beam on the inclined surface 201a resulting from the light beam made incident on the inclined surface 201a and the normal of the inclined surface 201a is set to α, the formula: cos θ=n·sin α is obtained from the formula: sin(π/2−θ)=n·sin α. Further, the formula: x=d/2·tan θ is obtained from the formula: (d/2)/x=tan θ. Further, from the formula: (d/2)/y=tan {π/2−(θ+α)}, a horizontal distance y between the position at which the light beam is made incident on the inclined surface 201a and the position at which the incident light beam is reflected by the upper surface of the prism 201 is obtained by the following formula.

$$y = d/2 \cdot \tan\{\pi/2 - (\theta+\alpha)\}$$

At this time, in order that the optical axis of the light beam, which is reflected on the upper surface of the prism 201 so as to be transmitted through the other inclined surface 201b to the outside of the prism 201, is the same as the optical axis of the light beam before it is first made incident on the inclined surface 201a, the formula: 1=2(x+y) must be established, where the length of the upper surface of the prism 201 is set to 1. Thus, the following formula is obtained.

$$1 = d \cdot [(1/\tan\theta) + (1/\tan\{\pi/2 - (\theta+\alpha)\}]$$
$$= d \cdot \{\tan(\pi/2 - \theta) + \tan(\theta+\alpha)\}$$

Therefore, the parameters of the trapezoidal prism 201 are specified by the following formulas (1) and (2) by using 1, d and θ.

$$1 = d \cdot \{\tan(\pi/2-\theta) + \tan(\theta+\alpha)\} \quad (1)$$

$$\alpha = \sin^{-1}\{(1/n)\cos\theta\} \quad (2)$$

Note that in the above embodiment, the aiming light beam Le emitted from the optical fiber FB8 is reflected by using the reflection mirror 105 so as to be guided into the fixed sleeve 38, but the aiming light beam Le may be made directly incident on the fixed sleeve 38 from the optical fiber FB8 via the collimator lens 107, without using the reflection mirror 105.

Figure 7:
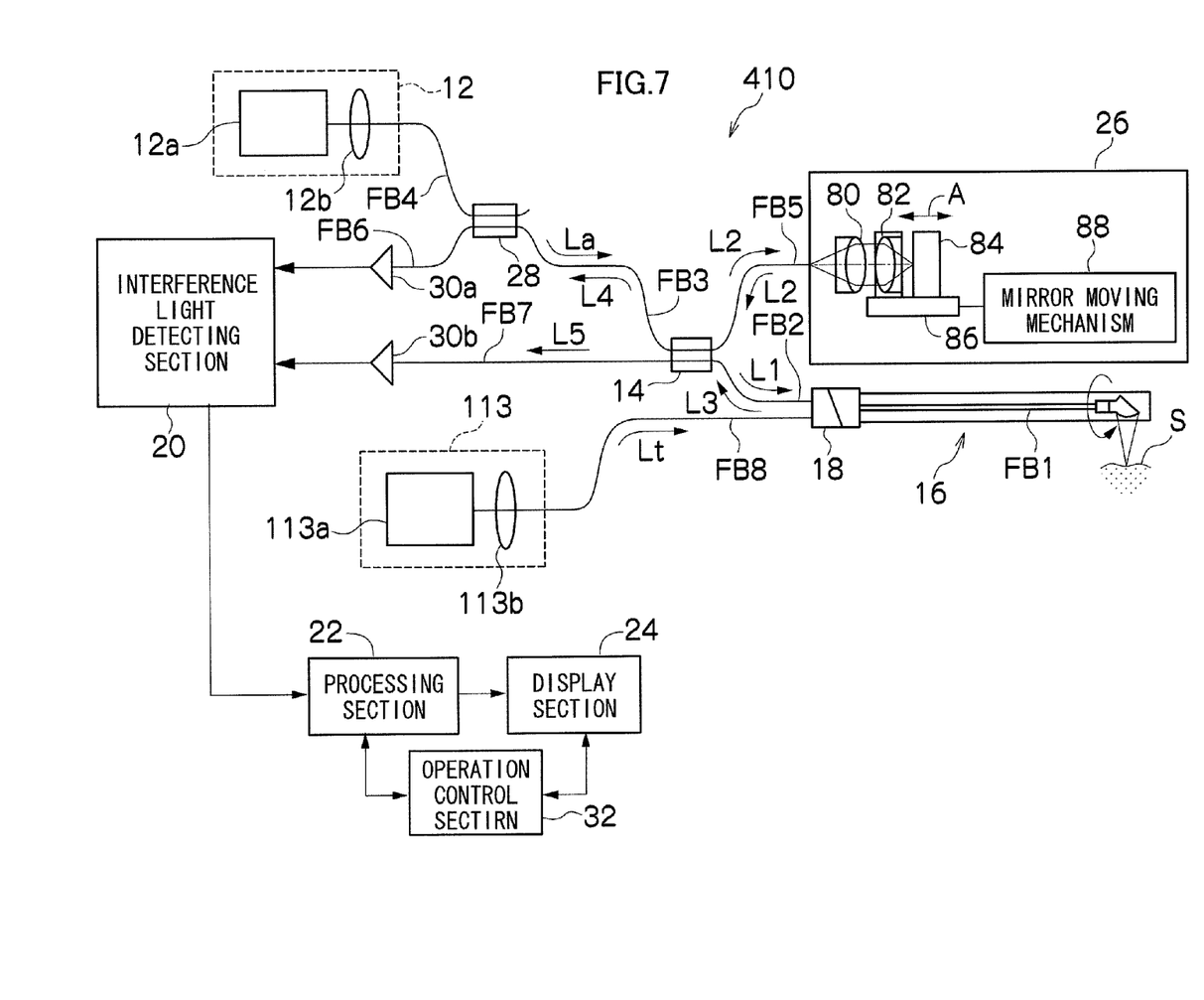
FIG. 7 shows a schematic configuration of an optical tomographic imaging apparatus according to a fourth embodiment.

Next, there will be described a fourth embodiment according to the present invention.

FIG. 7 shows a schematic configuration of an optical tomographic imaging apparatus according to the fourth embodiment.

As shown in FIG. 7, an optical tomographic imaging apparatus 410 according to the present embodiment is configured to multiplex an OCT signal light beam with a laser light beam for performing a thermal coagulation treatment or a photochemical treatment.

That is, in the optical tomographic imaging apparatus 410 according to the present embodiment, the first light source 12 emits the OCT signal light beam, while a second light source 113 emits the laser light beam for medical treatment.

The laser light beam emitted by the first light source 12 is a laser light beam having a wavelength of 1.3 μm which is the same wavelength as that used in the above described first embodiment, while the laser light beam emitted by the second light source 113 is exemplified, for example, by an Nd:YAG laser light beam having a wavelength of 1.06 μm, a high-output semiconductor laser light beam having a wavelength of 0.8 μm, or a red semiconductor laser light beam for photochemical treatment having a wavelength of 0.66 μm.

In this way, a laser light beam Lt for medical treatment emitted from the second light source 113 is made incident on the optical rotary adapter 18 via the optical fiber FB8, and is multiplexed, in the optical rotary adapter 18, with the measuring light beam L1 divided from the OCT signal light beam La emitted from the first light source 12.

The multiplexing method is not limited in particular, and one of the methods of the above described embodiments may be used. Note that the configuration in the present embodiment is the same as that of the above described first embodiment, except for the configuration in which the OCT signal light beam is multiplexed with the laser light beam for medical treatment.

In this way, it is possible to provide a configuration for both medical treatment and diagnosis by multiplexing the OCT signal light beam with the laser light beam for medical treatment.

Figure 8:
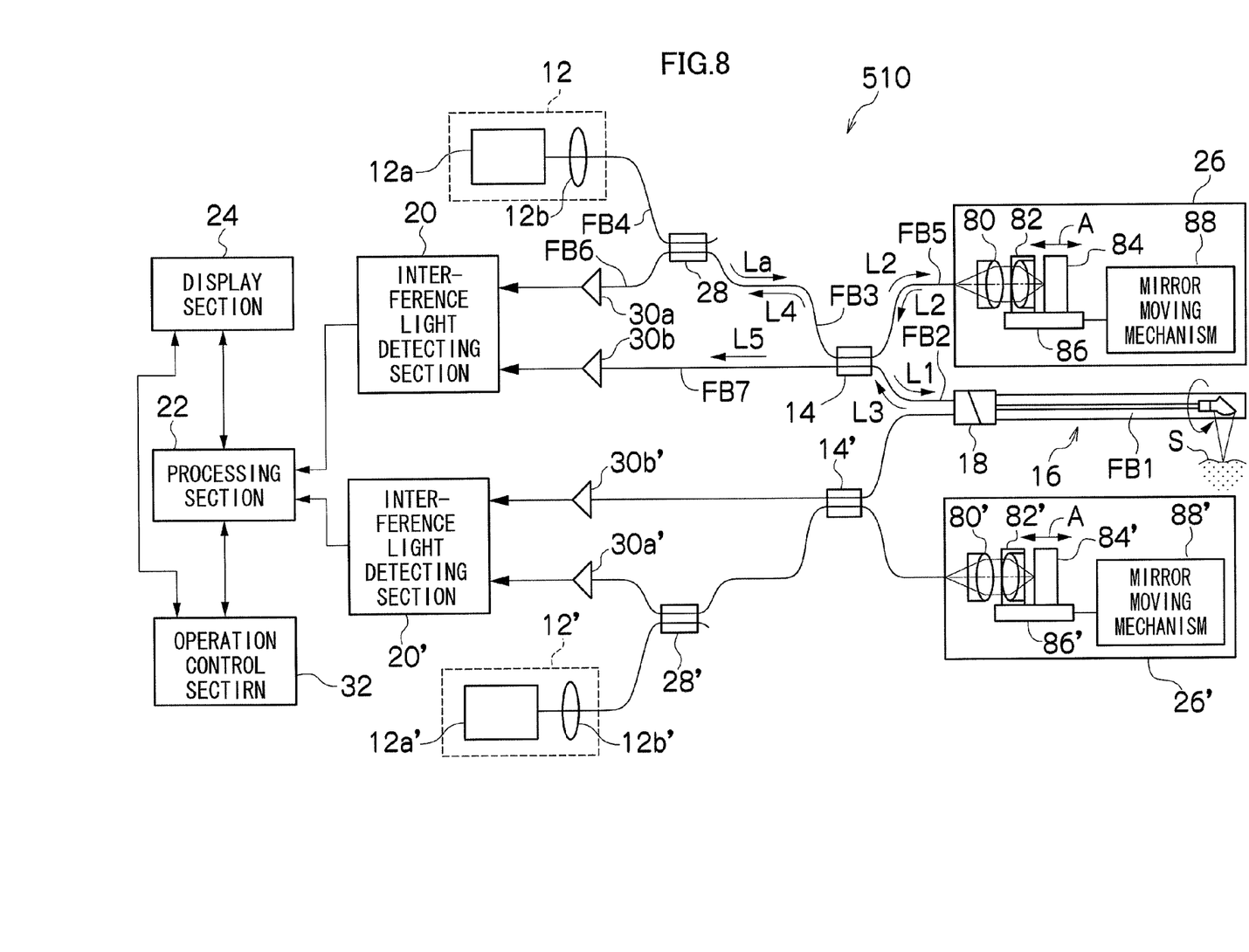
FIG. 8 shows a schematic configuration of an optical tomographic imaging apparatus according to a fifth embodiment.

Next, there will be described a fifth embodiment according to the present invention.

FIG. 8 shows a schematic configuration of an optical tomographic imaging apparatus according to the fifth embodiment.

As shown in FIG. 8, an optical tomographic imaging apparatus 510 according to the present embodiment includes two systems each of which performs measurement by emitting the OCT signal light beam.

Thereby, the wavelength band at the time of the measurement is expanded by multiplexing the two OCT signal light beams having different wavelengths, to thereby realize a multiple wavelength OCT apparatus.

As the two different OCT wavelengths, it is considered that the wavelength of 1.3 μm is used as before as the one of the two wavelengths, and that a wavelength of 1.06 μm, 0.8 μm or the like, is used as the other wavelength to be multiplexed with the wavelength of 1.3 μm.

As shown in FIG. 8, the OCT signal light beams having different wavelengths respectively emitted from two light sources 12 and 12' are multiplexed by the optical rotary adapter 18, and are guided into the optical probe 16 so that the measurement is performed. The embodiment shown in FIG. 8 is configured such that the interference of the return light beams is respectively detected by interference light detecting sections 20 and 20', and that the detection result is processed in the processing section 22 so as to be displayed as one image in the display section 24, but the configuration of the apparatus is not limited to this. The wavelengths to be multiplexed are not limited to two.

As describe above, it is possible to provide a configuration in which light beams to be multiplexed are connected by a fiber connector in an optical rotary joint section, and hence the light beams to be multiplexed can be simply changed. Therefore, it is considered that the scope of the present invention is not limited to the OCT image measurement, but that the scope of the present invention can also be extended to include a medical treatment apparatus having an OCT monitoring function by multiplexing not only the aiming light beam but also, for example, the light beam for medical treatment.

Further, the scope of the present invention can also be extended to include an OCT apparatus having multiple wavelengths by multiplexing OCT signal light beams having different wavelengths. Further, the number of the light beams to be multiplexed is not limited to two, and the present invention can also be applied to the case where three or more light beams are multiplexed.

In the above, there are described in detail the optical rotary adapter according to the present invention and the optical tomographic imaging apparatus using the optical rotary adapter. It is obvious that the present invention is not limited to the above described embodiments, and various modifications and variations are possible within the scope and spirit of the present invention.

What is claimed is:

1. An optical rotary adapter, comprising:
   a fixed sleeve;
   a fixed side optical fiber which is fixedly supported by the fixed sleeve and which has at one end thereof an end surface inclined by a predetermined angle with respect to a plane perpendicular to the optical axis of the optical fiber;
   a fixed side collimator lens which is arranged to be separated from the inclined end surface of the fixed side optical fiber by a predetermined interval;
   a rotary cylinder which is supported so as to be rotatable with respect to the fixed sleeve;
   a rotation side optical fiber which is fixedly supported substantially at the center of the rotary cylinder, which is arranged to face the fixed side collimator lens, and which has an end surface inclined by a predetermined angle with respect to a plane perpendicular to the optical axis of the fixed side collimator lens;
   a rotation side collimator lens which is fixedly supported by the rotary cylinder, and which is arranged between the fixed side collimator lens and the rotation side optical fiber so as to be separated from the inclined end surface of the rotation side optical fiber by a predetermined interval;
   a rotation drive device which rotationally drives the rotary cylinder;
   a second luminous flux optical fiber which guides a second luminous flux having a wavelength different from a wavelength of a first luminous flux as a measuring light beam to the inside of the fixed sleeve;
   a second luminous flux collimator lens which is arranged so as to be separated from the end surface of the second luminous flux optical fiber by a predetermined interval; and
   a multiplexing device which is provided between the fixed side collimator lens and the rotation side collimator lens in the fixed sleeve, and which multiplexes the first luminous flux and the second luminous flux.

2. The optical rotary adapter according to claim 1, wherein the multiplexing device includes at least one dichroic mirror which transmits one of the first luminous flux and the second luminous flux and which reflects the other luminous flux.

3. The optical rotary adapter according to claim 1, wherein the multiplexing device includes a device which, when the first luminous flux is multiplexed with the second luminous flux, compensates an optical axis shift so as to prevent the optical axis of the luminous flux after the multiplexing from being shifted from the optical axis of the first luminous flux before the multiplexing.

4. The optical rotary adapter according to claim 3, wherein the device which compensates the optical axis shift is configured by two inclined surfaces which are arranged substantially on the optical axis of the first luminous flux so as to face each other at respective angles having the same magnitude in the opposite directions.

5. The optical rotary adapter according to claim 3, wherein the device which compensates the optical axis shift is configured by a trapezoidal prism arranged substantially on the optical axis of the first luminous flux.

6. The optical rotary adapter according to claim 2, wherein an optical axis shift is compensated by offsetting beforehand the position of the fixed side optical fiber so that the optical axis of the luminous flux after the multiplexing is prevented from being shifted from the optical axis of the first luminous flux before the multiplexing.

7. The optical rotary adapter according to claim 1, wherein the second luminous flux is an aiming light beam serving as a measuring mark.

8. The optical rotary adapter according to claim 1, wherein the second luminous flux is a laser light beam for medical treatment.

9. The optical rotary adapter according to claim 1, wherein the second luminous flux is a measuring light beam having a wavelength different from the wavelength of the first luminous flux.

10. An optical tomographic imaging apparatus, which acquires an optical tomographic image of a measuring object, comprising:
- a first light source which emits a light beam for measurement;
- a second light source which emits a second luminous flux having a wavelength different from the wavelength of the light beam for measurement;
- a branching device which branches the light beam emitted from the first light source to a measuring light beam and a reference light beam;
- an optical probe including a rotation side optical fiber which guides the measuring light beam to the measuring object and which guides a return light beam from the measuring object, a measuring section which is arranged at the distal end section of the rotation side optical fiber and which irradiates the measuring object with the measuring light beam to acquire the return light beam from the measuring object, and a probe outer tube which covers the outer periphery of the rotation side optical fiber and the measuring section so as to rotatably support the rotation side optical fiber and the measuring section, and in which at least a region transmitting the measuring light beam from the measuring section and the return light beam from the measuring object is made of a transparent material;
- a fixed side optical fiber which guides the measuring light beam to the rotation side optical fiber and which guides the return light beam guided by the rotation side optical fiber;
- the optical rotary adapter according to claim 1, which rotatably connects the rotation side optical fiber to the fixed side optical fiber, which multiplexes the second luminous flux emitted from the second light source and guided by the second luminous flux optical fiber, with the first luminous flux as the measuring light beam, and which transmits the multiplexed luminous flux and the return light beam;
- a multiplexing section which multiplexes the return light beam detected by the measuring section and guided via the optical rotary adapter with the reference light beam, to generate an interference light beam;
- an interference light detecting section which detects the interference light beam as an interference signal; and
- a tomographic image acquiring section which acquires the optical tomographic image from the interference signal detected by the interference light detecting section.

* * * * *